Figure 1:
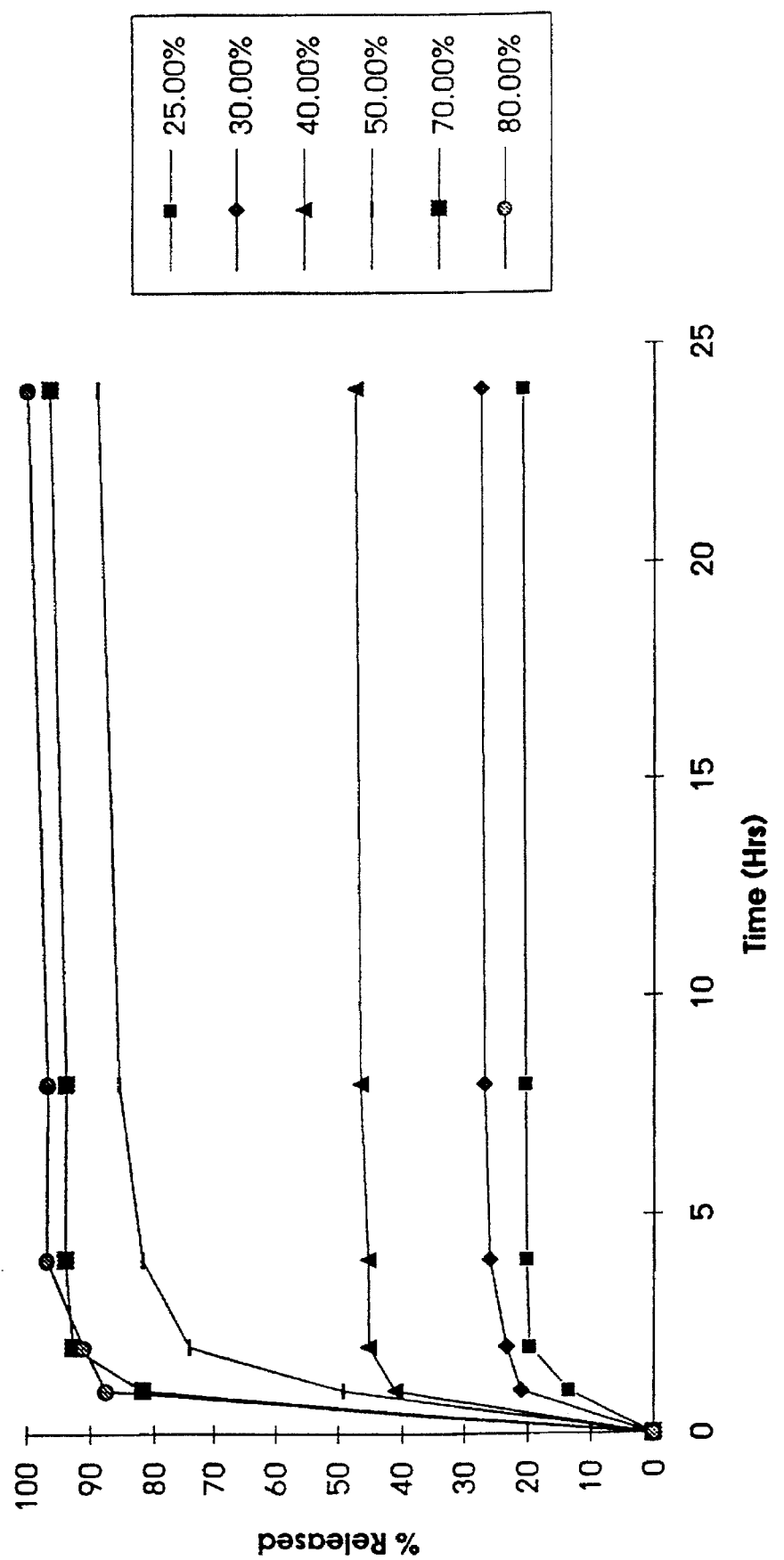

United States Patent [19]

Ramtoola

[11] Patent Number: 5,641,745
[45] Date of Patent: Jun. 24, 1997

[54] CONTROLLED RELEASE BIODEGRADABLE MICRO- AND NANOSPHERES CONTAINING CYCLOSPORIN

[75] Inventor: Zeibun Ramtoola, Dublin, Ireland

[73] Assignee: Elan Corporation, plc, Athlone, Ireland

[21] Appl. No.: 479,509

[22] Filed: Jun. 7, 1995

[30] Foreign Application Priority Data

Apr. 3, 1995 [IE] Ireland ..................................... 950233

[51] Int. Cl.$^6$ ........................... A61K 47/08; A61K 38/13
[52] U.S. Cl. .......................................... 514/11; 514/772.3
[58] Field of Search ................................. 530/300, 317, 530/321; 514/9, 11, 772, 772.3, 772.4, 772.5, 772.6, 772.7

[56] References Cited

U.S. PATENT DOCUMENTS

| | | | |
|---|---|---|---|
| 5,171,217 | 12/1992 | March et al. | 604/53 |
| 5,185,152 | 2/1993 | Peyman | 424/427 |
| 5,192,741 | 3/1993 | Orsolini et al. | 514/4 |
| 5,411,952 | 5/1995 | Kaswan | 514/11 |
| 5,415,864 | 5/1995 | Kopecek et al. | 424/436 |
| 5,468,503 | 11/1995 | Yamada et al. | 424/461 |

OTHER PUBLICATIONS

International Ophthalmology, vol. 17, No. 6, 1993, Harper et. al., "Bioavailability of microsphere . . . " pp. 337–340.
International Journal of Pharmaceutics, vol. 126, 1995, Chiu et al., "Effects of polymer degradation . . . " pp. 169–178.
Science, vol. 263, 1994, Gref et al., "Biodegradable Long–Circulating Polymeric Nanospheres", pp. 1600–1603.
Takada, K. et al, Biological and Pharmaceutical FActors Affecting the Absorption and Lymphatic Delivery of Cyclosporin A from Gastrointestinal Tract, *J. Pharmacobio-–Dyn.*, 11:80–7 (1988).

Fahr, A., Cyclosporin Clinical Pharmacokinetics, *Clin. Pharmacokinetics*, 24:472–95 (1993).

Drewe, J. et al., The Absorption Site of Cyclosporin in the Human Gastro–Intestinal Tract, *Br. J. Clin. Pharmac.*, 33:39–43 (1992).

Alonso, J., Poly)Lactic/Glycolic) Micro and Nanospheres As New Delivery Systems For Cyclosporin A., *Proceed. Intern. Symp. Control. Rel. Bioact. Mat.*, 20:109–10 (1993).

Ramtoola, Z., et al., Release Kinetics of Fluphenazine from Biodegradable Microspheres, *J. Microencapsulation*, 9:415–23 (1992).

*Primary Examiner*—Jeffrey E. Russel
*Assistant Examiner*—Kathleen Carroll
*Attorney, Agent, or Firm*—Mary L. Severson

[57] ABSTRACT

A controlled release pharmaceutical formulation which comprises cyclosporin entrapped in a biodegradable polymer to form microspheres or nanospheres such that the cyclosporin is substantially in an amorphous state and the biodegradable polymer comprises greater than 12.5% w/w poly(lactide). The biodegradable polymer is suitably poly-D,L-lactide or a blend of poly-D,L-lactide and poly-D,L-lactide-co-glycolide. Additionally, an enteric coating can be applied to the microspheres or nanospheres or to the oral dosage form incorporating the microspheres or nanospheres to protect the formulation while it passes through the stomach. A particularly suitable formulation comprises 50% w/w cyclosporin-loaded 80:20 blend of poly-D,L-lactide-co-glycolide to poly-D,L-lactide micro- and/or nanospheres. This formulation has the combined properties of nearly complete but relatively slow release of cyclosporin within 8 hours and is useful for targeting cyclosporin to the small intestine when administered orally.

20 Claims, 2 Drawing Sheets

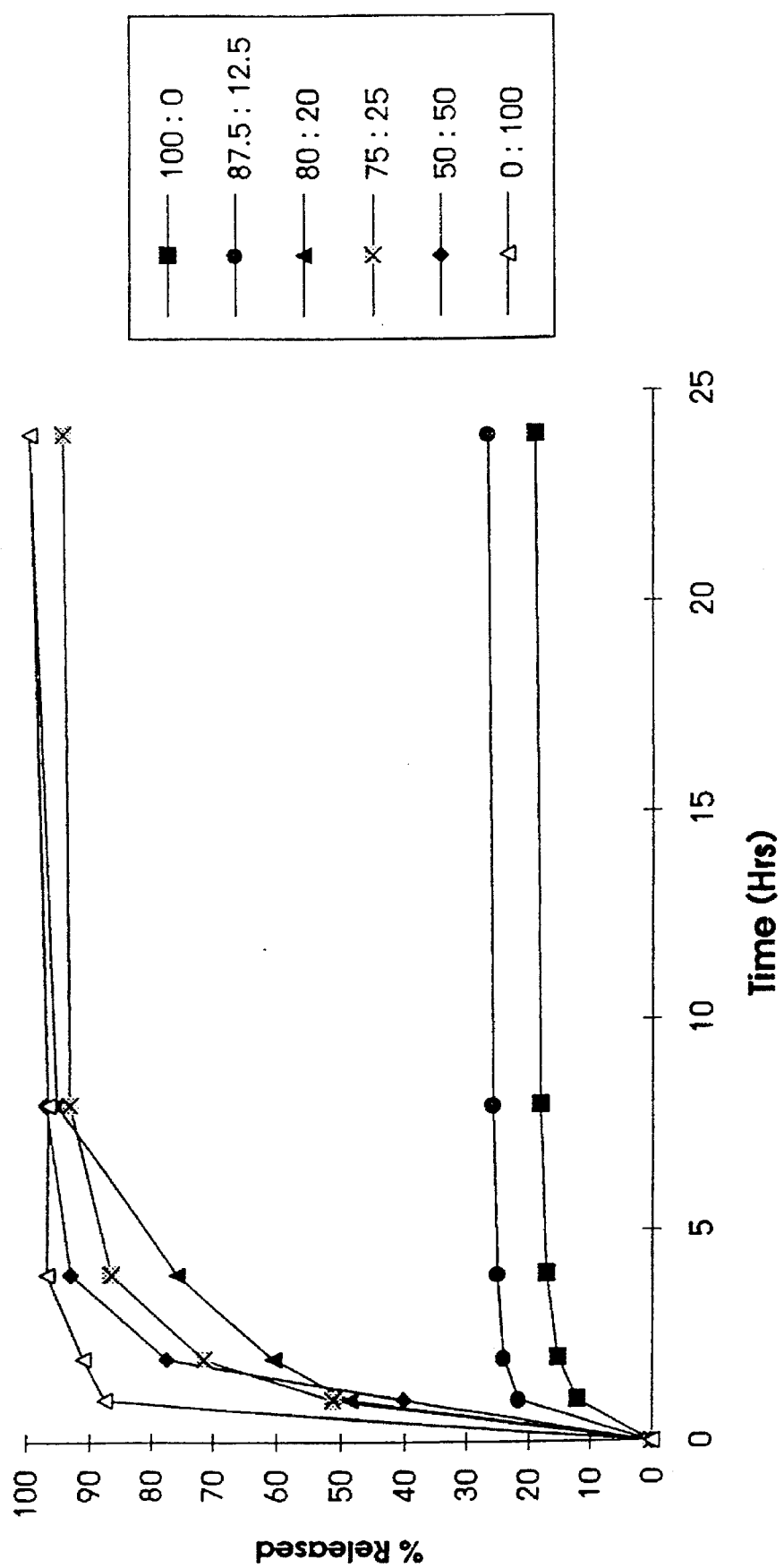

CONTROLLED RELEASE BIODEGRADABLE MICRO- AND NANOSPHERES CONTAINING CYCLOSPORIN

I. FIELD OF THE INVENTION

This invention relates to controlled release biodegradable micro- and nanosphere formulations and, in particular, biodegradable formulations containing cyclosporin or cyclosporin analogues.

II. BACKGROUND OF THE INVENTION

Cyclosporin A is a lipophilic cyclic undecapeptide of molecular weight 1203 isolated from the fungus *Tolypocladium inflatum* Gams which produces calcium dependent, specific and reversible inhibition of transcription of interleukin-2 and several other cytokines, most notably in T helper lymphocytes. Because of its immunosuppressive properties, it is widely used as first line therapy in the prophylaxis and treatment of transplant rejection and various autoimmune diseases. In patients with severe disease refractory to standard treatment, oral cyclosporin is an effective therapy in acute ocular Behcet's syndrome, endogenous uveitis, psoriasis, atopic dermatitis, rheumatoid arthritis, active Crohn's disease and nephrotic syndrome. This drug has also been used to treat patients with moderate or severe aplastic anaemia who are ineligible for bone marrow transplantation and those with primary biliary cirrhosis. Cyclosporin may be effective in patients with intractable pyoderma gangrenosum, polymyositis/dermatomyositis or severe, corticosteroid-dependent asthma. Cyclosporin is known to have a very specific effect on T-cell proliferation although the precise mechanism remains unclear. It has been shown to be an effective modifier of multidrug resistance in human and rodent cells. A number of non-immunosuppressive analogties of cyclosporin A have been shown to have resistance modifier activity and some are more potent than the parent compound.

Hypertrichosis, gingival hyperplasia and neurological and gastrointestinal effects are the most common adverse events in cyclosporin recipients. Also, changes in laboratory variables indicating renal dysfunction are relatively common.

Cyclosporin is highly lipophilic, poorly water soluble and, therefore, typically supplied as an olive oil or peanut oil solution for clinical use. However, the bioavailability of cyclosporin from such oily solutions is very low and gives rise to great intersubject variation with reported systemic availability ranging from 4 to 25% (Takada, K. et al, *J. Pharmacobio-Dyn.*, 11:80–7 (1988)). The bioavailability of cyclosporin has been reported to be dependent on food, bile and other interacting factors (Fahr, A., *Clin. Pharmacokinetics*, 24:472–95 (1993)). In a recent study in which a microemulsion preparation of cyclosporin was administered locally to different parts of the small and large intestine (duodenum, jejunum, ileum and colon descendens), cyclosporin was found to be absorbed predominantly in the small intestine (Drewe, J. et al., *Br. J. Clin. Pharmac.*, 33:39–43 (1992)).

Cyclosporin A has been encapsulated in poly-D,L-lactide-co-glycolide microspheres and nanospheres (Alonso, J., *Proceed. Intern. Symp. Control. Rel. Bioact. Mat.*, 20:109–10 (1993)). However, these microspheres and nanospheres failed to release more than 50% of the entrapped cyclosporin within a 28 day period.

Thus, to address the toxicity and intra- and intersubject variation in availability issues, there exists a need for a cyclosporin pharmaceutical formulation with increased bioavailability. Further, there exists a need for a cyclosporin formulation which efficiently targets cyclosporin to the absorption site(s) for cyclosporin.

III. SUMMARY OF THE INVENTION

Surprisingly, this invention discloses that release of cyclosporin from poly(lactide) microspheres or nanospheres is considerably higher than release from corresponding poly(lactide-co-glycolide) microspheres or nanospheres. This increase in release, and subsequent bioavailability, is correlated with cyclosporin being present in a substantially amorphous form in the poly(lactide) formulations as opposed to the presence of crystalline cyclosporin in the poly(lactide-co-glycolide) formulations. Thus, this invention provides cyclosporin-containing microspheres or nanospheres that are capable of releasing greater than 80%, preferably greater than 90%, of the entrapped drug within an 8 hour period in a controlled fashion. When these microspheres or nanospheres are orally administered to a subject, particularly a human, the release of cyclosporin in the stomach is minimized to avoid bioavailability variations due to the presence of food, bile or other factors. However, the release of cyclosporin is targeted to the small intestine, the site at which cyclosporin is predominantly absorbed.

In particular, this invention provides a controlled release pharmaceutical formulation, which comprises cyclosporin entrapped in a biodegradable polymer to form microspheres or nanospheres, wherein the cyclosporin is substantially in an amorphous state and wherein the biodegradable polymer comprises greater than 12.5% w/w poly(lactide).

The biodegradable polymer is suitably poly-D,L-lactide or a blend of poly-D,L-lactide and poly-D,L-lactide-co-glycolide, provided that the blend contains enough poly(lactide) so that the entrapped cyclosporin is substantially in an amorphous state.

The controlled release pharmaceutical formulation of this invention suitably has a dissolution profile measured under sink conditions at 37° C. for cyclosporin substantially as follows:

a) 40–80% release within 1 hour;

b) 75–95% release within 4 hours; and c) $\geq 80\%$ within 8 hours.

Thus, this invention provides cyclosporin-containing microspheres or nanospheres that are capable of releasing greater than 80%, preferably greater than 90%, of the entrapped drug within an 8 hour period in a controlled fashion. When these microspheres or nanospheres are orally administered to a subject, particularly a human, the release of cyclosporin in the stomach is minimized to avoid bioavailability variations due to the presence of food, bile or other factors. However, the release of cyclosporin is targeted to the small intestine, the site at which cyclosporin is predominantly absorbed.

The biodegradable micro- and nanospheres preferably contain 25 to 80% w/w cyclosporin, more especially 45–55% w/w cyclosporin.

A particularly suitable formulation comprises 50% w/w cyclosporin-loaded 80:20 w/w blend of poly-D,L-lactide-co-glycolide to poly-D,L-lactide micro- and/or nanospheres. This formulation has the combined properties of nearly complete but relatively slow release of cyclosporin within 8 hours and is useful for targeting cyclosporin to the small intestine when administered orally.

The micro- and nanospheres in accordance with the invention are suitably incorporated into oral dosage forms, such as capsules, tablets, powders including powders capable of effervescing upon addition of water, or suspensions. Additionally, an enteric coating can be applied to the microspheres or nanospheres or to the oral dosage form to protect the formulation while is passes through the stomach to further target release of cyclosporin to the small intestine. Alternatively, the micro- and nanospheres in accordance with the invention can be administered parenterally to release greater than 80%, preferably greater than 90%, of the entrapped cyclosporin in a controlled manner over an 8 hour period.

Thus, for convenient and effective oral administration, effective amounts of the micro- and/or nanospheres of this invention can be tabletted with one or more excipient(s), encased in capsules such as gel capsules, formulated with ingredients which, upon addition of water, provide an effervescent solution, and suspended in a liquid solution and the like. The micro- and nanospheres can be suspended in a saline solution or the like for parenteral administration.

It will be appreciated that the pharmaceutical formulations in accordance with the invention can be used inter alia to provide immunosuppression in organ transplant patients and to treat autoimmune diseases. Suitably, a therapeutic amount of the formulation of this invention is administered to humans such that the whole blood levels of cyclosporin A are maintained between 200 and 500 mg/mL, which currently is believed to be the levels at which serious renal toxicity is unusual. Thus, a suitable dose of the formulation of this invention is less than 5 mg/kg/day of cyclosporin entrapped in the micro- or nanospheres.

IV. BRIEF DESCRIPTION OF THE DRAWINGS

FIG. 1 shows the increasing release of cyclosporin from cyclosporin-loaded poly-D,L-lactide microspheres as the drug loading is increased from 25% to 30% to 40% to 50% to 70% to 80% (w/w); and FIG. 2 shows the unexpected greater release of cyclosporin from cyclosporin-loaded poly-D,L-lactide microspheres or poly-D,L-lactide:poly-D,L-lactide-co-glycolide microspheres in which the cyclosporin is predominantly in the amorphous state (i.e., microspheres having a poly-D,L-lactide-co-glycolide to poly-D,L-lactide ratio of w/w 0:100, 50:50, 75:25 and 80:20) as opposed to the slower release from cyclosporin-loaded microspheres in which crystalline cyclosporin is present (i.e., microspheres having a poly-D,L-lactide-co-glycolide to poly-D,L-lactide w/w ratio of 87.5:12.5 and 100:0).

V. DETAILED DESCRIPTION OF THE INVENTION

As used herein, the term "cyclosporin" refers to cyclosporin A and analogues of cyclosporin A having similar physical properties.

As used herein, the term "biodegradable" as applied to polymers means polymers which are degradable in vivo either enzymatically or non-enzymatically to produce biocompatible or non-toxic by-products which can be further metabolized or excreted via normal physiological pathways. Examples of synthetic biodegradable polymers include poly (lactide); poly(glycolide) and poly(lactide-co-glycolide), steroisomers (i.e., D, L), racemic mixtures, and polymer mixtures thereof.

Biodegradable micro- and nanospheres containing 25 to 80% w/w cyclosporin (Leiras) are suitably prepared herein by a solvent evaporation/extraction procedure from an emulsion system (Ramtoola, Z. et al., *J. Microencapsulation,* 9:415–23 (1992)). The polymers used are suitably poly-D,L-lactide having a MW of 16,000 and i.v. of 0.2 dl/g (R-203; Boehringer Ingelheim) and poly-D,L-lactide-co-glycolide 50:50 of i.v. 0.5 dl/g (RG-504; Boehringer Ingelheim).

For instance, cyclosporin and the encapsulating polymer are dissolved in methylene chloride. Suitable methylene chloride to polymer ratios are 1–2 ml methylene chloride/g of R-203 and 3 ml of methylene chloride/g of RG-504. This drug/polymer solution is then suitably emulsified in an aqueous PVA solution (suitably 0.27%) in a ratio of about 10 ml of the drug/polymer solution to 100 ml of the PVA solution and mixed at high speed (suitably 20,000–24,000 rpm) for 2 min followed by stirring at 1000 rpm for 2 hr. The particles are recovered by centrifugation and dried overnight in a vacuum oven.

In the following Examples, the particles produced were characterized by scanning electron microscopy (S360, Leica, Cambridge) and were sized using a Malvern 2600 Laser Sizer. The particles were also characterized by X-ray diffraction (Daco-MP 500, Siemens). The drug content of the microparticles was assayed by HPLC using a Novapak C8 column at 70° C. using a mobile phase of acetronitrile-:water:methanol: phosphoric acid (900:525:75:0.075) at a flow rate of 2 ml/min with UV detection at 210 nm.

The solubility of cyclosporin was measured at 37° C. in increasing concentrations of sodium lauryl sulfate (SLS) solutions to determine sink conditions for dissolution studies. As was expected, the solubility of cyclosporin (S) was found to increase linearly with increasing SLS concentration (M) according to the following equation:

$$S=S_0+K\cdot M$$

where $S_0$ is the intrinsic solubility of cyclosporin and K is the solubilizing capacity. A value of 0.284 with a correlation coefficient of 0.997 was obtained for K and an SLS concentration of ≧0.3% (w/v) was found to provide sink conditions. In vitro release studies of the cyclosporin were carried out, under sink conditions, using a VanKel dissolution bath and dissolution samples were analyzed by HPLC.

The invention will be further illustrated by the following Examples.

EXAMPLE 1

Cyclosporin-loaded poly-D,L-lactide microspheres

The characteristics of cyclosporin-loaded microparticles prepared in the manner described above using R-203 as the encapsulating polymer (emulsion mixed at 20,500 rpm for 2 min) are shown in Table 1. The drug entrapment efficiency of the particles produced was independent of the drug loading and was higher than 93% in all cases. Photomicrographs show the surface of the particles produced to be smooth and drag free for this range of drag loadings. Scanning electron microscopy showed the particles to be below 5 microns in diameter. Particle size analysis gave larger $D_{50\%}$ values for the particles, probably a result of particle aggregation during this measurement. X-ray diffraction of the microspheres showed that cyclosporin was present in an amorphous state for all of these drug loadings.

TABLE 1

| Sample | Starting Drug Loading (w/w %) | Assayed Drug Loading (w/w %) | Entrapment Efficiency (%) | $D_{50}$ (μm) |
|---|---|---|---|---|
| CYC1 | 25 | 25.97 | 103.88 | 19.20 |
| CYC2 | 30 | 38.39 | 127.97 | 8.43 |
| CYC3 | 40 | 37.40 | 93.50 | 17.50 |
| CYC4 | 50 | 46.86 | 93.72 | 24.98 |
| CYC5 | 70 | 66.54 | 95.06 | 5.76 |
| CYC6 | 80 | 79.67 | 99.59 | 10.88 |

The release of cyclosporin from the microparticles was found to be faster the higher the drug loading and is shown in FIG. 1. An initial burst in release, which increased with increasing drug loading, was observed for all systems studied. This burst effect is usually associated with drug located at or near the surface of the microsphere and would be expected to increase with increasing drag loading of the microspheres. Cyclosporin release was consistent with a diffusion controlled mechanism at the higher drug loadings (>40%). At low drug loadings, initial release (over the first 24 hours) was by diffusion. Subsequent cyclosporin release from the microspheres was slower and probably controlled by polymer degradation.

EXAMPLE 2

Cyclosporin-loaded poly-D,L-lactide-co-glycolide: poly-D, L-lactide microspheres Cyclosporin-loaded microspheres at the 50% w/w drug loading were prepared in the manner described above using the more hydrophilic RG-504 polymer and various blends of RG-504 and R-203 (emulsion mixed at 24,000 rpm for 2 min) as shown in Table 2. Similar to the poly-D,L-lactide microspheres, photomicrographs showed the surface of all particles produced to be smooth and drug free and with a diameter of less than 5 microns. The drug entrapment efficiency was found to be independent of the polymer blend used and was greater than 79.5%. In contrast to the poly-D,L-lactide microspheres, X-ray diffraction of the 100% poly-D,L-lactide-co-glycolide microspheres and those having up to 12.5% w/w poly-D,L-lactide revealed the presence of crystalline cyclosporin.

TABLE 2

| Sample | Starting Drug Loading (w/w %) | Assayed Drug Loading (w/w %) | Entrapment Efficiency (%) | Ratio RG504:R203 |
|---|---|---|---|---|
| CYC7 | 50 | 53.08 | 106.16 | 100:0 |
| CYC8 | 50 | 50.60 | 101.20 | 87.5:12.5 |
| CYC9 | 50 | 42.62 | 85.24 | 83.5:16.5 |
| CYC10 | 50 | 39.76 | 79.52 | 80:20 |
| CYC11 | 50 | 50.42 | 100.84 | 75:25 |
| CYC12 | 50 | 52.44 | 104.88 | 50:50 |
| CYC13 | 50 | 55.86 | 111.72 | 0:100 |

The release of cyclosporin from the more hydrophilic poly-D,L-lactide-co-glycolide microspheres was slower than for corresponding microspheres prepared with poly-D, L-lactide as shown in FIG. 2. The initial burst effect with the blended polymers was lower than that observed with the pure poly-D,L-lactide and was found to increase with increasing poly-D,L-lactide content. As the ratio of the more hydrophobic R-203 was increased in the polymer blend, the release of cyclosporin was found to increase with a marked increase in dissolution rate when the poly-D,L-lactide content increased from 12.5% to 20% w/w.

The slower release of cyclosporin from the poly-D,L-lactide-co-glycolide microspheres was unexpected because poly-D,L-lactide-co-glycolide is more hydrophilic and is therefore more easily wetted than poly-D,L-lactide. However, because cyclosporin is a hydrophobic drug, it may form a molecular dispersion in the hydrophobic poly-D,L-lactide matrix, giving rise to a higher initial burst effect and the faster release profiles observed. The X-ray diffraction data for the poly-D,L-lactide particles showing the encapsulated cyclosporin to be in an amorphous state compared to the presence of crystalline cyclosporin in the more hydrophilic microspheres (i.e., microspheres containing up to 12.5% w/w poly-D,L-lactide) can explain the unexpected slower drug release observed from these more hydrophilic microspheres.

What is claimed is:

1. A controlled release pharmaceutical formulation, which comprises cyclosporin entrapped in a biodegradable polymer to form microspheres or nanospheres, wherein the cyclosporin is substantially in an amorphous state and-wherein the biodegradable polymer comprises 100% poly (lactide) or a blend of polymers comprising greater than 12.5% w/w poly(lactide).

2. A controlled release pharmaceutical formulation according to claim 1, wherein the biodegradable polymer is poly-D,L-lactide.

3. A controlled release pharmaceutical formulation according to claim 1, wherein the biodegradable polymer is a blend of poly-D,L-lactide and poly-D,L-lactide-co-glycolide.

4. A controlled release pharmaceutical formulation according to claim 1, wherein the dissolution profile measured under sink conditions comprising an aqueous $\geq 0.3$ (w/v) sodium lauryl sulfate solution at 37° C. for cyclosporin is substantially as follows:

a) 40–80% release within 1 hour;

b) 75–95% release within 4 hours; and c) $\geq 80\%$ within 8 hours.

5. A controlled release pharmaceutical formulation according to claim 1, further comprising an enteric coating on the microspheres or nanospheres to target release of cyclosporin to the small intestine.

6. A controlled release pharmaceutical formulation according to claim 1, wherein the drug loading of the microspheres or nanospheres ranges from about 20% to 80% w/w.

7. A controlled release pharmaceutical formulation according to claim 1, wherein the microspheres or nanospheres are formulated as capsules, tablets, powders, powders capable of effervescing upon addition of water, or suspensions.

8. A controlled release pharmaceutical formulation according to claim 7, wherein the microspheres or nanospheres are formulated as tablets and further comprising an enteric coating on the tablet to target release of cyclosporin to the small intestine.

9. A controlled release pharmaceutical formulation according to claim 1, wherein the drug loading of the microspheres or nanospheres ranges from 45 to 55% w/w and the biodegradable polymer is a 20:80 w/w blend of poly-D,L-lactide to poly-D,L-lactide-co-glycolide.

10. A method of enhancing the bioavailability of cyclosporin in a subject, comprising administering to the subject a therapeutic amount of a controlled release pharmaceutical formulation comprising cyclosporin entrapped in a biodegradable polymer to form microspheres or nanospheres, wherein the cyclosporin is substantially in an amorphous state and wherein the biodegradable polymer comprises 100% poly(lactide) or a blend of polymers comprising greater than 12.5% w/w poly(lactide).

11. A method according to claim 10, wherein the biodegradable polymer is poly-D,L-lactide.

12. A method according to claim 10 wherein the biodegradable polymer is a blend of poly-D,L-lactide and poly-D,L-lactide-co-glycolide.

13. A method according to claim 10, wherein the formulation further comprises an enteric coating on the microspheres or nanospheres to target release of cyclosporin to the small intestine.

14. A method according to claim 10, wherein the drug loading of the microspheres or nanospheres ranges from about 20% to 80% w/w.

15. A method according to claim 10, wherein the microspheres or nanospheres are formulated as capsules, tablets, powders, powders capable of effervescing upon addition of water, or suspensions.

16. A method according to claim 15, wherein the microspheres or nanospheres are formulated as tablets and wherein the tablet is coated with an enteric coating to target release of cyclosporin to the small intestine.

17. A method according to claim 10, wherein the drug loading of the microspheres or nanospheres ranges from 45 to 55% w/w and the biodegradable polymer is a 20:80 w/w blend of poly-D,L-lactide to poly-D,L-lactide-co-glycolide.

18. A method of targeting cyclosporin to the small intestine of a subject to minimize bioavailability variations of the cyclosporin, comprising orally administering to the subject a therapeutic amount of a controlled release pharmaceutical formulation comprising cyclosporin entrapped in a biodegradable polymer to form microspheres or nanospheres, wherein the cyclosporin is substantially in an amorphous state and wherein the biodegradable polymer comprises 100% poly(lactide) or a blend of polymers comprising greater than 12.5% w/w poly(lactide).

19. A method according to claim 18, wherein the formulation further comprises an enteric coating on the microspheres or nanospheres to further target release of cyclosporin to the small intestine.

20. A method according to claim 18, wherein the microspheres or nanospheres are formulated as tablets and wherein the tablet is coated with an enteric coating to target release of cyclosporin to the small intestine.

* * * * *